(12) United States Patent
Srinivasa et al.

(10) Patent No.: US 11,596,320 B2
(45) Date of Patent: Mar. 7, 2023

(54) BLOOD PULSE MEASUREMENT BASED ON CAPACITIVE SENSING

(71) Applicant: Texas Instruments Incorporated, Dallas, TX (US)

(72) Inventors: Murali Srinivasa, Sunnyvale, CA (US); Scott Douglas Kulchycki, Mountain View, CA (US); David Zakharian, San Francisco, CA (US); Preeti Rajendran, Mountain View, CA (US)

(73) Assignee: Texas Instruments Incorporated, Dallas, TX (US)

(*) Notice: Subject to any disclaimer, the term of this patent is extended or adjusted under 35 U.S.C. 154(b) by 1040 days.

(21) Appl. No.: 14/462,159

(22) Filed: Aug. 18, 2014

(65) Prior Publication Data
US 2015/0051468 A1 Feb. 19, 2015

Related U.S. Application Data

(60) Provisional application No. 61/866,808, filed on Aug. 16, 2013.

(51) Int. Cl.
*A61B 5/0245* (2006.01)
*A61B 5/024* (2006.01)
(Continued)

(52) U.S. Cl.
CPC ........ *A61B 5/0245* (2013.01); *A61B 5/02438* (2013.01); *A61B 5/02444* (2013.01); *A61B 5/053* (2013.01); *A61B 5/6803* (2013.01)

(58) Field of Classification Search
None
See application file for complete search history.

(56) References Cited

U.S. PATENT DOCUMENTS

| | | | | |
|---|---|---|---|---|
| 4,561,447 A | * | 12/1985 | Kawamura | A61B 5/021 600/500 |
| 7,128,714 B1 | * | 10/2006 | Antonelli | A61B 5/021 600/485 |

(Continued)

FOREIGN PATENT DOCUMENTS

DE 102011112226 A1 * 5/2013 ............. B60N 2/002

OTHER PUBLICATIONS

DE102011112226A1—English Translation.*
(Continued)

*Primary Examiner* — Jacqueline Cheng
*Assistant Examiner* — Jairo H Portillo
(74) *Attorney, Agent, or Firm* — Valerie M. Davis; Frank D. Cimino

(57) ABSTRACT

A capacitive sensing system is adapted for noninvasive measurement of blood pulse (hear rate). A capacitive sensor is located near a skin pulse point exhibiting pulse displacement of skin tissue from vascular pulsation (for example, the temple area of the head), and includes a sensor electrode disposed over and spaced from the skin pulse point, such that the distance between sensor electrode and the skin pulse point cycles between a proximal and a distal displacement distance based on vascular pulsation. A capacitance-to-digital conversion (CDC) unit includes excitation circuitry providing sensor excitation to generate a sensor E-field between the sensor electrode and the skin pulse point based on sensor self-capacitance, and capacitance acquisition/conversion circuitry that acquires capacitance measurements for proximal and distal self-capacitance (for example, by multi-phase capacitive charge transfer using a switched capacitor arrangement), and converts these capacitance measurements into sensor data representative of vascular pulsation.

22 Claims, 3 Drawing Sheets

(51) Int. Cl.
*A61B 5/053* (2021.01)
*A61B 5/00* (2006.01)

(56) References Cited

U.S. PATENT DOCUMENTS

| | | | | |
|---|---|---|---|---|
| 7,935,061 B1* | 5/2011 | Breed | ............ | A61B 5/021 |
| | | | | 600/485 |
| 8,271,262 B1* | 9/2012 | Hsu | ............ | A61B 5/05 |
| | | | | 704/206 |
| 2002/0099286 A1* | 7/2002 | Sandler | ............ | A61B 7/026 |
| | | | | 600/407 |
| 2004/0249293 A1* | 12/2004 | Sandler | ............ | A61B 7/00 |
| | | | | 600/481 |
| 2006/0125623 A1* | 6/2006 | Appelt | ............ | A61B 5/02055 |
| | | | | 340/521 |
| 2008/0021332 A1* | 1/2008 | Brainard, III | ...... | A61B 5/02416 |
| | | | | 600/483 |
| 2009/0043229 A1* | 2/2009 | Dunn | ............ | A61B 5/442 |
| | | | | 600/587 |
| 2009/0159343 A1* | 6/2009 | Chung | ............ | G06F 3/045 |
| | | | | 178/18.05 |
| 2009/0306536 A1* | 12/2009 | Ranganathan | ............ | A61B 5/01 |
| | | | | 600/549 |
| 2010/0079384 A1* | 4/2010 | Grivna | ............ | G06F 3/0443 |
| | | | | 345/173 |
| 2010/0113952 A1* | 5/2010 | Raguin | ............ | G06K 9/0012 |
| | | | | 600/509 |
| 2011/0208071 A1* | 8/2011 | Lu | ............ | A61B 5/0285 |
| | | | | 600/500 |
| 2012/0139562 A1* | 6/2012 | Beyly | ............ | G06F 3/044 |
| | | | | 324/679 |
| 2012/0254244 A1* | 10/2012 | Vetek | ............ | G06K 9/00315 |
| | | | | 707/780 |
| 2012/0265080 A1* | 10/2012 | Yu | ............ | A61B 5/6893 |
| | | | | 600/509 |
| 2013/0057660 A1* | 3/2013 | Kim | ............ | A61B 5/743 |
| | | | | 348/51 |
| 2013/0120310 A1* | 5/2013 | Siska | ............ | H03K 17/962 |
| | | | | 345/174 |

OTHER PUBLICATIONS

Mari, B., et al. "Analysis of temporal artery biopsies in an 18-year period at a community hospital." European journal of internal medicine 20.5 (2009): 533-536. (Year: 2009).*

* cited by examiner

BLOOD PULSE MEASUREMENT BASED ON CAPACITIVE SENSING

CROSS-REFERENCE TO RELATED APPLICATIONS

Priority is claimed under USC § 119(e) to: (a) U.S. Provisional Application 61/866,808, filed 16 Aug. 2013.

BACKGROUND

Technical Field

This Patent Document relates generally to noninvasive measurement of blood flow, such as for measuring blood pulse (heart rate).

Related Art

The vascular system of blood vessels (arteries, veins and capillaries) circulate blood continuously, directed by the pulsatile rhythm of the heart. Each cardiac cycle creates a pressure wave (change in blood volume), or pulse, that propagates through the vasculature.

Arteries and veins provide two means of measuring blood flow: pressure and pulse or heart rate. Pulse is manifested as a rhythmic expansion and recoil of elastic arteries and veins. This pulsation is more pronounced in arteries, which carry blood pumped out of the heart.

Pulse points are areas of the body where an artery is relatively near the skin surface, permitting the external examination (detection, measurement) of arterial pulse. Example pulse points are the carotid artery in the neck branching to the temporal (superficial) artery at the temple, and the radial and ulnar branches of the brachial artery running down the forearm through the wrist. Palpation (touch) is the common method of examining arterial pulse, and pulse points are also referred to as compression/pressure points susceptible to palpation.

At some pulse points, arterial pulse is also manifest as skin vibration caused by the pulse waves propagating through the vasculature. At these pulse points, the arterial vibrations associated with arterial expansion/recoil (displacement) are not entirely absorbed by overlying tissue layers, and appear as skin vibration/displacement (on the order of a hundreds of microns).

BRIEF SUMMARY

This Brief Summary is provided as a general introduction to the Disclosure provided by the Detailed Description and Figures, summarizing certain aspects and features of the disclosed invention. It is not a complete overview of the Disclosure, and should not be interpreted as identifying key elements or features of the invention, or otherwise characterizing or delimiting the scope of the invention disclosed in this Patent Document.

The Disclosure describes apparatus and methods for capacitive sensing adaptable for noninvasive measurement of pulsation of a blood vessel within a body. The methodology is operable in a capacitive sensing system including a capacitive sensor, including a sensor electrode and a sensor shield, disposed in proximity to a skin pulse point exhibiting pulse displacement of skin tissue caused by pulsation of the blood vessel (vascular pulsation). The capacitive sensor includes a sensor electrode disposed over and spaced from the skin pulse point, such that the distance between sensor electrode and the skin pulse point cycles between a proximal and a distal distance based on vascular pulsation, where the proximal distance corresponds to a proximal pulse displacement, and the distal distance corresponds to a distal pulse displacement. The sensor shield is disposed over and insulated from the sensor electrode.

Aspects and features of the methodology for noninvasive capacitive measurement of vascular pulsation include: (a) exciting the sensor electrode to generate a sensor E-field between the sensor electrode and the skin pulse point based on sensor self-capacitance; (b) driving sensor shield to generate a shield E-field such that the sensor E-field is concentrated in the direction of the skin pulse point; (c) acquiring capacitance measurements for a proximal self-capacitance of the sensor electrode with the skin pulse point at proximal displacement, and a distal self-capacitance of the sensor electrode with the skin pulse point at distal displacement; and (d) converting the proximal and distal capacitances into sensor data representative of vascular pulsation.

Other aspects and features of the methodology include capacitive sensing base on multi-phase capacitive charge transfer in which: (a) sensor excitation is at an excitation frequency with excitation/charging and transfer/discharging phases; and (b) capacitance measurements are acquired by charging the sensor electrode during the excitation/charging phase, and discharging the capacitor during the transfer/discharging phase. In addition, the shield E-field can be generated by driving the sensor shield to generate the shield E-field with substantially the same polarity and phase as the sensor E-field.

In one application of the methodology for noninvasive capacitive measurement of vascular pulsation, the capacitive sensor is adapted for amalgamation with an arm of a pair of spectacles, such that the sensor electrode is locatable in proximity to skin pulse point at a superficial temporal artery.

Other aspects and features of the invention claimed in this Patent Document will be apparent to those skilled in the art from the following Disclosure.

DETAILED DESCRIPTION

This Description and the Figures disclose example embodiments and applications that illustrate various features and advantages of the invention, aspects of which are defined by the Claims. Known circuits, functions and operations are not described in detail to avoid unnecessarily obscuring the principles and features of the invention.

In brief overview, a capacitive sensing system can be adapted for noninvasive measurement of vascular pulsation. The capacitive sensing system includes a capacitive sensor and a capacitance-to-digital conversion (CDC) unit.

The capacitive sensor is disposed external to the body in proximity to a skin pulse point exhibiting pulse displacement of skin tissue caused by pulsation of the blood vessel (vascular pulsation), and a body capacitance. The capacitive sensor includes a sensor electrode and a driven sensor shield. The sensor electrode is disposed over and spaced from the skin pulse point, such that the distance between sensor electrode and the skin pulse point cycles between a proximal and a distal distance based on vascular pulsation, where the proximal distance corresponds to a proximal pulse displacement, and the distal distance corresponds to a distal pulse displacement. The sensor shield disposed over and insulated from the sensor electrode.

The CDC unit is coupled to the capacitive sensor, and configured to convert sensor capacitance into sensor data representative of the vascular pulsation. The CDC unit includes excitation circuitry and capacitance acquisition/conversion circuitry. The excitation circuitry is configured to provide sensor excitation to excite the sensor electrode, generating a sensor E-field between the sensor electrode and the skin pulse point based on sensor self-capacitance, and provide shield drive to drive the sensor shield to generate a shield E-field such that the sensor E-field is concentrated in the direction of the skin pulse point. The capacitance acquisition/conversion circuitry is configured to acquire capacitance measurements for a proximal self-capacitance of the sensor electrode with the skin pulse point at proximal displacement, and a distal self-capacitance of the sensor electrode with the skin pulse point at distal displacement, and convert the proximal and distal self-capacitance measurements into sensor data representative of vascular pulsation.

Figure 1:
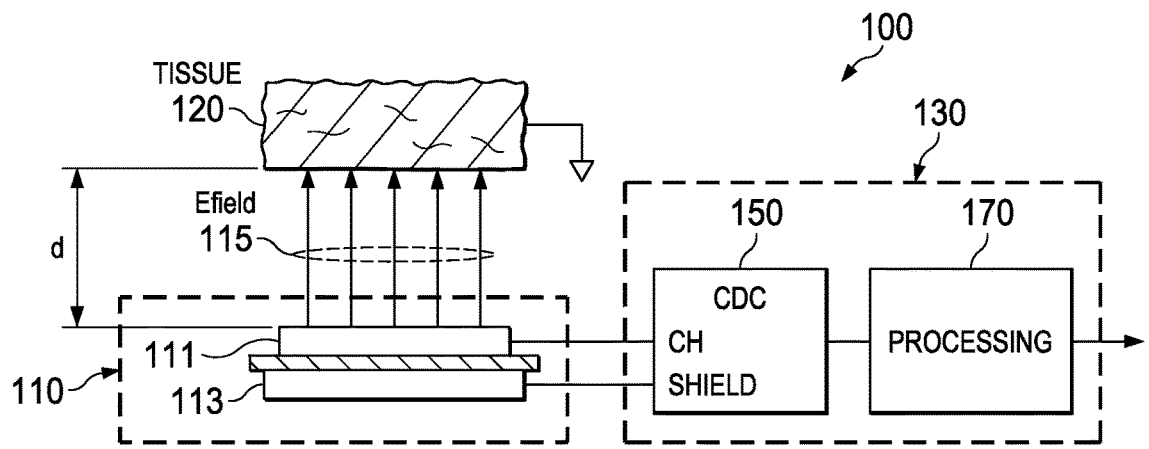
FIG. 1 is an example functional illustration of a capacitive sensing system adapted for noninvasive sensing of blood pulse (heart rate), including a sensor capacitive sensor adapted for location in proximity to a skin pulse point exhibiting pulse displacement of skin tissue caused by vascular pulsation, and including a capacitance-to-digital conversion (CDC) unit with sensor and shield drivers, and capacitance conversion of capacitance readings into sensor capacitance data corresponding to vascular pulsation (proximal capacitance associated with the sensor electrode and the body capacitance at proximal displacement, and distal capacitance associated with the sensor electrode and body capacitance for distal displacement).

FIG. 1 is an example functional illustration of a capacitive sensing system 100 adapted for noninvasive sensing/measurement of blood pulse (heart rate). Capacitive sensing system 100 includes a capacitive sensor 110 and capacitance acquisition/conversion 130 formed by a capacitance-to-digital conversion (CDC) unit 150, and a data processor 170. These components need not be co-located, but to reduce the effects of parasitic capacitance, CDC 150 is preferably located as close as possible to capacitive sensor 110.

Capacitive sensing system 100 is configure for capacitive sensing based on projected self-capacitance.

CDC 150 acquires self-capacitance measurements from capacitive sensor 110, and converts these capacitance measurements to digital sensor data representative of vascular pulsation. The CDC sensor data can be input to data processor 170, and processed to provide pulse (heart rate) information.

Capacitive sensor 110 includes a sensor electrode 111 and a sensor shield 113. Capacitive sensor 110 is configured for projected self-capacitance. Capacitive sensor 10 is adapted for location at the body 120, in proximity to a skin pulse point, exhibiting pulse displacement of skin tissue caused by pulsation of the blood vessel (vascular pulsation). Body 120 exhibits the physical property of body capacitance.

Pulse points are areas of the body where a blood vessel, typically an artery, is relatively near the skin surface, permitting the external measurement of arterial pulse. Example pulse points are the carotid artery in the neck branching to the temporal (superficial) artery at the temple, and the radial and ulnar branches of the brachial artery that run down the forearm through the wrist.

Figure 2A:
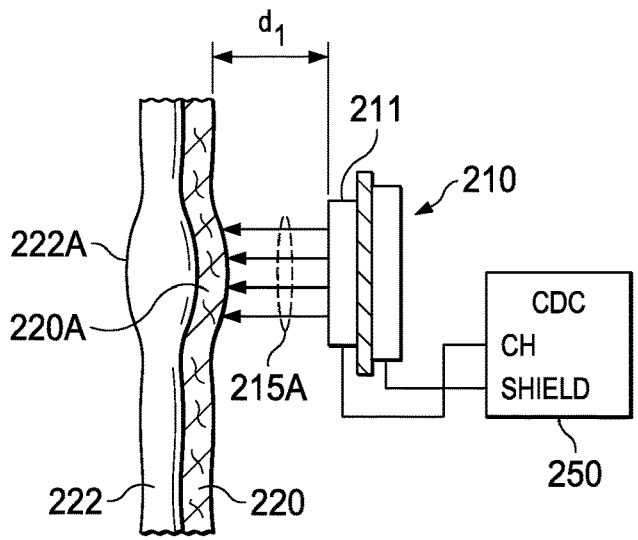
FIGS. 2A/2B illustrate a capacitive sensor disposed at a skin pulse point for a blood vessel, exhibiting pulse displacement of skin tissue caused by vascular pulsation, cycling between respectively a proximal and a distal sensing distance: (2A) illustrates proximal pulse displacement caused by vascular expansion; and (2B) illustrates distal pulse displacement caused by vascular recoil.

FIGS. 2A/2B illustrate a capacitive sensor located in proximity to an area of the body 220 in which an artery 222 is at a skin pulse point 220A/222A. Skin pulse point 220A/222A exhibits pulse displacement of skin tissue caused by vascular pulsation, cycling between respectively a proximal and a distal sensing distance.

Capacitive sensor 210 includes a sensor electrode 211 disposed over and spaced from the skin pulse point 220A/220B by an air gap, such that the distance d1/d2 between the sensor electrode and the skin pulse point cycles between a proximal d1 and a distal d2 distance based on vascular pulsation 222A/222B.

FIG. 2A illustrates a skin pulse point 220A/222A in which a proximal pulse displacement d1 is caused by vascular expansion. While some of this vascular expansion will be absorbed by the skin tissue 220A, some will appear at the skin surface as a proximal expansion, corresponding to the vascular expansion 222A, resulting in a proximal pulse displacement distance d1 between surface of skin 220A and sensor electrode 211.

Figure 2B:
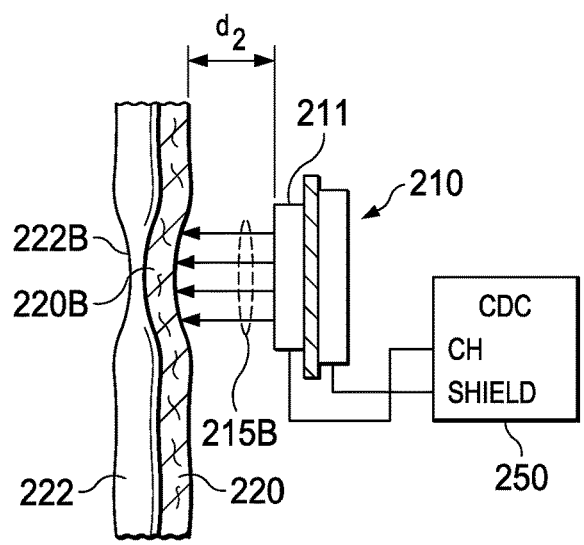

FIG. 2B illustrates a skin pulse point 220B/222B in which a distal pulse displacement d2 is caused by vascular recoil. While some of this vascular recoil will be absorbed by the skin tissue 220B, some will appear at the skin surface as a distal recoil, corresponding to the vascular recoil 222B, resulting in a distal pulse displacement distance d2 between the surface of skin 220B and sensor electrode 211.

Referring to FIG. 1, capacitive sensor 110 includes a sensor electrode 111 disposed over and spaced from the skin pulse point (FIGS. 2A/B, 220A/222A and 220B/222B) by an air gap, such that the distance d between sensor electrode 111 and the skin pulse point cycles between a proximal and a distal distance based on vascular pulsation. In FIG. 2A, the proximal distance d1 corresponds to a proximal pulse displacement 222A, and in FIG. 2B, the distal distance d2 corresponds to a distal pulse displacement 222B.

Capacitive sensor 110 includes a driven sensor shield 113, also coupled to a shield driver in CDC 150. Sensor shield 113 is disposed over, and insulated from, sensor electrode 111.

CDC 150 is coupled to capacitive sensor 110 through an acquisition channel, including sensor excitation, and including sensor shield drive. CDC 150 captures sensor capacitance, acquiring sensor capacitance measurements, which are converted sensor data representative of the vascular pulsation. CDC 150 includes sense excitation and shield drive.

CDC 150 includes excitation circuitry and capacitance acquisition/conversion circuitry. CDC 150 provides sense excitation to excite sensor electrode 111 to generate a sensor E-field between the sensor electrode and the skin pulse point based on sensor self-capacitance (FIGS. 2A/B, 220A/222A and 220B/222B). CDC 150 can be configured to drive the sensor shield to generate a shield E-field such that the sensor E-field is concentrated in the direction of the skin pulse point. For example, shield drive can be configured to generate the shield E-field with substantially the same polarity and phase as the sensor E-field.

The CDC capacitance acquisition/conversion circuitry captures capacitance measurements from sensor electrode 111 corresponding to vascular pulsation. CDC 150 performs capacitance acquisition to acquire capacitance measurements for a proximal self-capacitance of the sensor electrode with the skin pulse point at proximal displacement (FIG. 2A, 220A/222B), and a distal self-capacitance of the sensor electrode with the skin pulse point at distal displacement (FIG. 2B, 220V/222B).

In one implementation, CDC 150 can be configured for acquisition/conversion based on multi-phase capacitive charge transfer in which sensor excitation at a specified excitation frequency with excitation/charging and transfer/discharging phases, and capacitance acquisition involves acquiring capacitance measurements based on capacitive charge transfer (charging the sensor capacitor during the excitation/charging phase, and discharging the sensor electrode during the transfer/discharging phase).

CDC 150 converts the proximal and distal self-capacitance measurements into sensor data representative of vascular pulsation. CDC 150 outputs the sensor data for processing by data processor, such as to determine pulse (heart rate) information.

Figure 3:
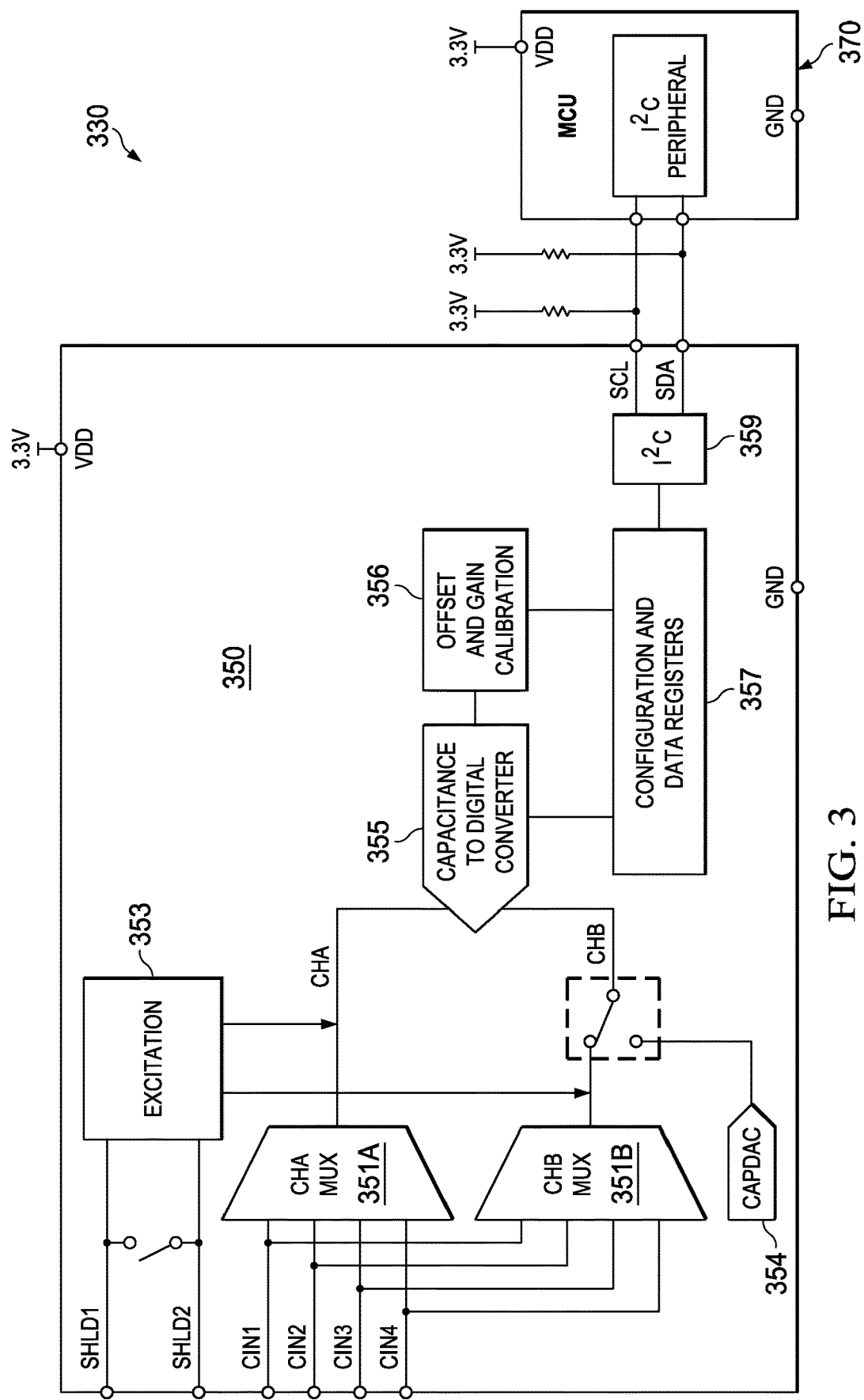
FIG. 3 illustrates an example embodiment of a multi-channel CDC unit that implements capacitance-to-digital conversion, with sensor excitation and shield drive for focusing the sensor E-field, capacitance capture for proximal capacitance associated with the sensor electrode and the body capacitance at proximal displacement, and distal capacitance associated with the sensor electrode and body capacitance for distal displacement, and data conversion of the sensor capacitance readings as sensor capacitance data corresponding to vascular pulsation.

FIG. 3 illustrates an example embodiment of a CDC unit 350 and data processor 370 implemented in an MCU (microcontroller unit). CDC 350 implements capacitance-to-digital conversion, with capacitance acquisition of proximal and distal capacitance measurements, and conversion to sensor capacitance data corresponding to vascular pulsation.

CDC 350 includes four input/acquisition channels CIN1-4 and two shield drive channels SHLD1-2. Capacitance (positive and/or negative) is measured between CINx and GND (an example input capacitance range is 0 pF to 15 pF). The CINx channel inputs are multiplexed by channel multiplexers 351A/B into dual acquisition/measurement channels CHA/CHB. CDC 350 is configurable for single-ended (CHA) or differential (CHA/CHB) capacitance measurement.

CDC 350 implements capacitance acquisition/measurement based on multi-phase capacitive charge transfer, such as with a switched capacitor configuration. Excitation block 353 is configured to provide sensor excitation and shield drive. Sensor excitation is provided at a specified excitation frequency for capacitive charge transfer (with excitation/charging and transfer/discharging phases). Shield drive can be provided synchronously with sensor excitation frequency, and can be used to focus sensing direction, and to counteract CINx parasitic capacitance.

Sensor excitation at the excitation frequency generates a sensor E-field between the sensor electrode and the skin pulse point based on sensor self-capacitance. During the excitation/charging phase, a sense voltage is applied to CINx, charging the sensor electrode. During the transfer/discharging phase the sensor electrode is discharged into a designated acquisition channel CHA/CHB, transferring charge that is a measure of the self-capacitance of the capacitive sensor.

Specifically, CDC 350 measures proximal self-capacitance of the sensor electrode with the skin pulse point at proximal displacement (FIG. 2A, 220A/222A), and distal self-capacitance of the sensor electrode with the skin pulse point at distal displacement (FIG. 2A, 220B/222B).

Excitation block can be configured to drive the sensor shield to the same voltage as CINx (i.e., at the sensor excitation frequency), so that any capacitance between the CINx and SHLDx pins does not affect CINx charge transfer. That is, SHLD1-2 can be driven so that the shield E-field is at substantially the same polarity and phase as the sensor E-field. SHLD1 is used to shield channels coupled to acquisition CHA (through multiplexer 351A), and SHLD2 is used to shield channels coupled to acquisition CHB (through multiplexer 351B). In a single ended configuration, SHLD1 is shorted to SHLD2. If a shielded cable is used for sensor connection, the cable shield should be connected to the SHLDx pins.

CAPDAC 354 can be used to balance common-mode or offset capacitance. CAPDAC provides a negative capacitance with a programmable resolution, connected internally to the CINx pins (Sensor Data≈(CINx or CINy)−CAPDAC)). For example, CAPDAC 354 can be used for programmable shifting of the input range, adding a programmable offset capacitance, enabling input capacitance measurements in the range of 0 pF to 15 pF with an offset capacitance up to 100 pF.

CDC 350 includes a capacitance-to-digital converter, offset and gain calibration 356, and configuration and data registers 357.

Converter 355 performs capacitance acquisition and data conversion. Converter 355 measures CHA/CHB input/acquisition capacitance, subject to CAPDAC offset, based on analog charge transfer. Specifically, sensor capacitance measurements (proximal/distal self-capacitance) are acquired through phased charge transfer, such as with a switched capacitor arrangement. Converter 355 performs analog-to-digital conversion, converting the sensor self-capacitance measurements into digital data, such as with a sigma delta converter. Configuration and Data Registers 357 includes data registers used in conjunction with capacitance capture (acquisition/conversion) by converter 355.

Offset and gain calibration 356 can provide offset calibration coefficient(s) for parasitic capacitance offset calibration, which can be combined with offset provided by the on-chip CAPDACs 354, and gain calibration used to normalize capacitance measurements of the CINx input channels based on stored gain coefficient(s). Configuration and Data Registers 357 includes configuration registers that store configuration values for offset/gain calibration. Offset registers can store digitized capacitance values (for example, in the range of −16 pF to +16 pF) which can be added to each channel to remove parasitic capacitance due to external circuitry, including tuning offset capacitance provided by CAPDACs 354. Gain registers can store gain factor correction (for example, in the range of 0 to 4) which can be applied to each channel in order to remove gain mismatch due to external circuitry.

CDC 350 can be configured for interfacing to a single-ended, or dual differential capacitive sensors. For single-ended configurations, CDC 350 is coupled to a single-ended capacitive sensor through input CINx and GND—in this configuration SHLD1 is internally shorted to SHLD2. For differential configurations, interfaced to a differential capacitive sensor with dual sensors, CDC 350 measures differential, unbalanced capacitance at CINx within the input capacitance range (for example, 15 pF). In this configuration the SHLD1 signal operates with CHA, and the SHLD2 signal operates with CHB. CAPDAC is disabled.

CDC 350 can be configured to support two modes of operation, single acquisition and repeated acquisition. In single acquisition mode, only one capacitance acquisition/measurement is enabled. CDC 350 is configured for appropriate acquisition parameters (repeat bit=0, and, for example, sample rate and notch filter), and an acquisition is performed by capturing the capacitance measurement, storing the result in a register and setting a measurement-done bit. In repeated acquisition mode, CDC 350 performs cycled acquisitions. CDC 350 is configured for appropriate acquisition parameters (repeat bit=1 and repeat value, and, for example, sample rate, notch filter), and an acquisition is performed by capturing the designated number of capacitance measurements, storing the results in a register and setting a measurement-done bit. Cycled acquisition remains on until the repeat bit is set to "0".

Results can be transferred to data processor 370 in a read operation. The results in the capacitance measurement registers 357 can be cyclically updated even if the registers are not read.

CDC 330 can be interfaced to an MCU processor 370, such as through an I2C interface. Sensor data captured into data registers 357 is output to the MCU processor 370, for processing as vascular pulse information.

Figure 4:
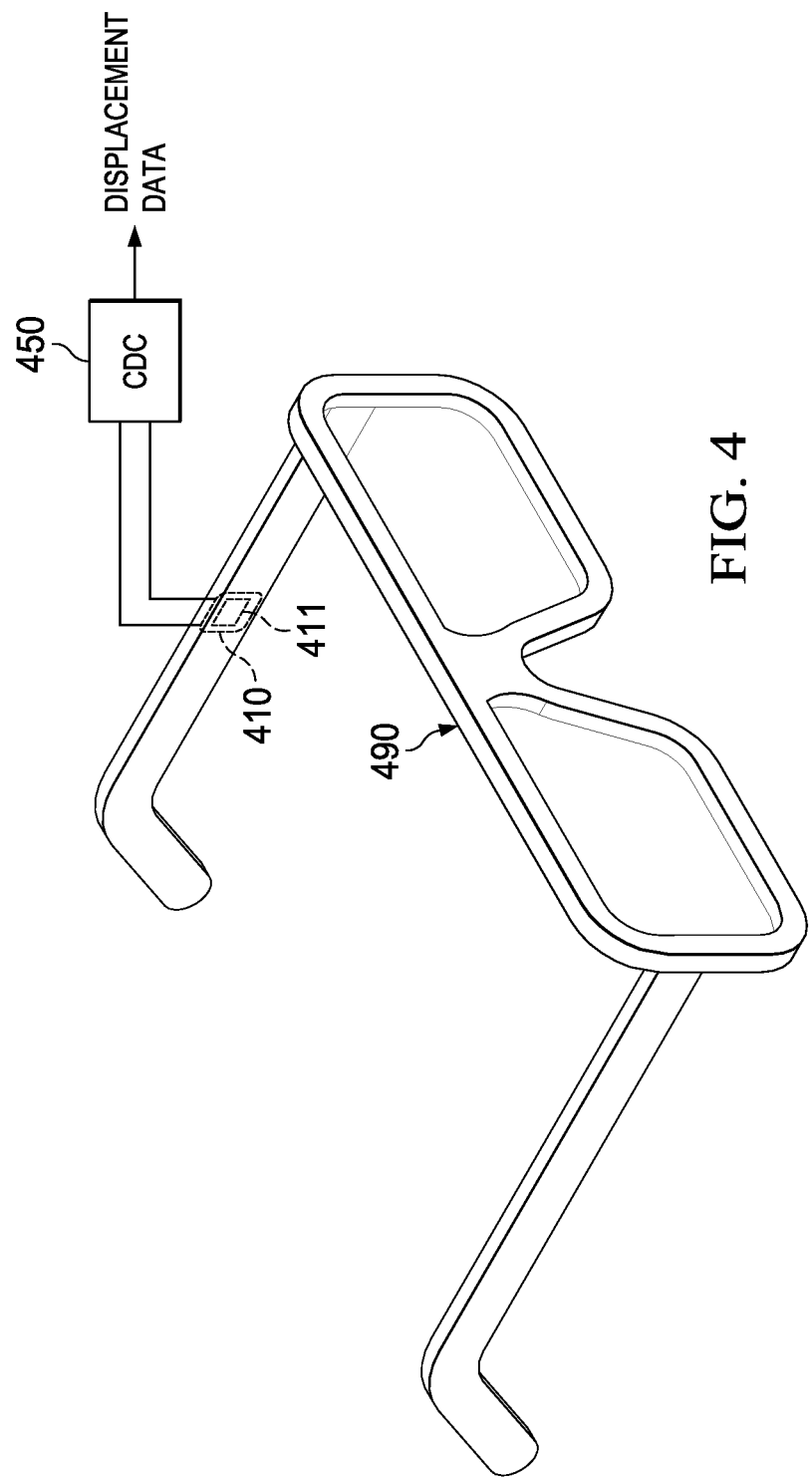
FIG. 4 illustrates an example embodiment of a capacitive sensor integrated into a sensor structure adapted for attachment to (or other amalgamation with) an arm of a pair of spectacles, that when worn locates the sensor in proximity to a temple, near a temporal (superficial) artery.

FIG. 4 illustrates an example embodiment of a capacitive sensor 410, including a sensor electrode 411, adapted for amalgamation with an arm of a pair of spectacles 490. For example, sensor 410 can be integrated into a pulse sensing structure adapted for attachment to the spectacles arm—the pulse sensing structure can also integrate a CDC unit, co-located with capacitive sensor 410, along with wireless communication to a data processor. When worn, spectacles 490 locate sensor 410 in proximity to a temple, near a skin pulse point at a temporal (superficial) artery.

The Disclosure provided by this Description and the Figures sets forth example embodiments and applications, including associated operations and methods, that illustrate various aspects and features of the invention. These example embodiments and applications may be used by those skilled in the art as a basis for design modifications, substitutions and alternatives to construct other embodiments, including adaptations for other applications, Accordingly, this Description does not limit the scope of the invention, which is defined by the Claims.

The invention claimed is:

1. A method comprising:
   determining a first capacitance at a first distance between skin and a surface of a capacitive sensor, in which the surface is spaced a first distance from the skin, the determining of the first capacitance including exciting an electrode of the capacitive sensor to charge the capacitive sensor and to generate an electric field between the electrode and the skin based on self-capacitance;
   determining a second capacitance at a second distance between the skin and the surface of the capacitive sensor, the second distance being greater than the first distance, the determining of the second capacitance including exciting the electrode to charge the capacitive sensor and to generate an electric field between the electrode and the skin based on self-capacitance, the first and second capacitances representing vascular pulsation of a blood vessel at a pulse point; and
   converting the first and second capacitances into data representing the vascular pulsation.

2. The method of claim 1, further comprising:
   determining a measurement of blood flow using the data representing the vascular pulsation.

3. The method of claim 2, wherein determining the measurement of blood flow includes determining heart rate.

4. The method of claim 2, wherein determining the measurement of blood flow includes determining pulse.

5. The method of claim 1, wherein the data representing the vascular pulsation includes digital data.

6. The method of claim 1, wherein:
   the first capacitance represents a vascular expansion of the blood vessel; and
   the second capacitance represents a vascular recoil of the blood vessel.

7. The method of claim 1, wherein the first and second capacitances represent vascular pulsation of a superficial temporal artery at the temple.

8. The method of claim 1, wherein the first and second capacitances represent vascular pulsation of a brachial artery at the wrist.

9. The method of claim 1, wherein:
   determining the first and second capacitances includes discharging the capacitive sensor using analog charge transfer to capture the first and second capacitances.

10. The method of claim 9, wherein converting the first and second capacitances into the data includes converting the first and second capacitances into digital data.

11. The method of claim 1, further comprising driving a sensor shield of the capacitive sensor to focus the electric field toward the pulse point.

12. An apparatus comprising:
    a capacitive sensor including an electrode having first and second opposite surfaces, the second surface adapted to be positioned closer to the skin than the first surface; and
    a converter coupled to the capacitive sensor, the converter configured to:
       determine a first capacitance sensed at a first distance between the second surface of the electrode and the skin; and
       determine a second capacitance sensed at a second distance between the second surface of the electrode and the skin, the second distance being greater than the first distance, the first and second capacitances representing vascular pulsation of a blood vessel at a pulse point; and
       convert the first and second capacitances into data representing the vascular pulsation,
    wherein, in determining each of the first and second capacitances, the converter is further configured to excite the electrode to charge the capacitive sensor and generate an electric field between the electrode and the skin based on self-capacitance.

13. The apparatus of claim 12, wherein the capacitive sensor further includes:
    a sensor shield insulated from the sensor electrode.

14. The apparatus of claim 12, further comprising:
    a processor coupled to the converter, the processor configured to determine a measurement of blood flow using the data representing the vascular pulsation.

15. The apparatus of claim 12, wherein the converter includes an analog-to-digital converter configured to convert the first and second capacitances into digital data representing the vascular pulsation.

16. The apparatus of claim 15, wherein the converter further includes:

a multiplexer having inputs coupled to the capacitive sensor and an output coupled to the analog-to-digital converter.

17. The apparatus of claim 16, wherein the multiplexer is a first multiplexer having first inputs, and the converter further includes:
a second multiplexer having second inputs coupled to the capacitive sensor and to the first inputs of the first multiplexer, the second multiplexer further having a respective output coupled to the analog-to-digital converter.

18. Spectacles that includes the apparatus of claim 12.

19. A system comprising:
a capacitive sensor including an electrode;
excitation circuitry coupled to the capacitive sensor and configured to provide excitation and shield drive signals to the capacitive sensor;
a multiplexer having inputs coupled to the electrode;
a capacitive-to-digital converter coupled to an output of the multiplexer, the capacitive-to-digital converter configured to:
determine a first capacitance sensed at a first distance between a surface of the electrode and skin; and
determine a second capacitance sensed at a second distance between the surface of the electrode and the skin, the first and second capacitances representing vascular pulsation of a blood vessel at a pulse point; and
convert the first and second capacitances into digital data representing the vascular pulsation;
wherein, in determining each of the first and second capacitances, the capacitive-to-digital converter is further configured to excite the electrode to charge the capacitive sensor and generate an electric field between the electrode and the skin based on self-capacitance.

20. The system of claim 19, wherein the multiplexer is a first multiplexer having first inputs, and the system further comprising:
a second multiplexer having second inputs coupled to the electrode and respectively coupled to the first inputs of the first multiplexer, the second multiplexer further having a respective output coupled to the capacitive-to-digital converter.

21. The system of claim 19, further comprising a processor coupled to the capacitive-to-digital converter, the processor configured to determine a measurement of blood flow using the digital data representing the vascular pulsation.

22. The system of claim 19, wherein the capacitive-to-digital converter is configured to determine a first plurality of capacitances at the first distance and a second plurality of capacitances at the second distance and convert the first and second plurality of capacitances into digital data representing the vascular pulsation.

\* \* \* \* \*